(12) United States Patent
Makela et al.

(10) Patent No.: US 8,846,114 B1
(45) Date of Patent: Sep. 30, 2014

(54) COMPOSITION FOR THE TREATMENT OF HERPES AND COLD SORES

(71) Applicant: Oleavicin, LLC, Santa Barbara, CA (US)

(72) Inventors: Craig Makela, Goleta, CA (US); Cindy Makela, Goleta, CA (US)

(73) Assignee: Oleavicin, LLC, Goleta, CA (US)

(*) Notice: Subject to any disclaimer, the term of this patent is extended or adjusted under 35 U.S.C. 154(b) by 0 days.

(21) Appl. No.: 14/018,629

(22) Filed: Sep. 5, 2013

(51) Int. Cl.
| | |
|---|---|
| *A01N 65/00* | (2009.01) |
| *A61K 31/4166* | (2006.01) |
| *A61K 36/38* | (2006.01) |
| *A61K 36/886* | (2006.01) |
| *A61K 36/61* | (2006.01) |
| *A61K 35/02* | (2006.01) |
| *A61K 36/63* | (2006.01) |
| *A61K 31/045* | (2006.01) |

(52) U.S. Cl.
CPC ............ *A61K 36/63* (2013.01); *A61K 31/4166* (2013.01); *A61K 36/38* (2013.01); *A61K 36/886* (2013.01); *A61K 36/61* (2013.01); *A61K 35/02* (2013.01); *A61K 31/045* (2013.01)
USPC ........................................................ 424/725

(58) Field of Classification Search
None
See application file for complete search history.

(56) References Cited

U.S. PATENT DOCUMENTS 5,997,876 A * 12/1999 Shikhashvili et al. ........ 424/730

* cited by examiner

*Primary Examiner* — Michael Meller
(74) *Attorney, Agent, or Firm* — Marc E. Hankin; Anooj M. Patel; Kevin Schraven

(57) ABSTRACT

A composition for treating herpes and cold sores. The composition may be topically applied, ingested into the body, or injected into the body. The composition may be applied quickly and discretely in order to sooth and treat herpes and cold sores. The composition utilizes a highly effective combination of compounds, including *olea europaea* leaf extract and *olea europaea* fruit oil, to achieve this end.

3 Claims, No Drawings

COMPOSITION FOR THE TREATMENT OF HERPES AND COLD SORES

FIELD OF INVENTION

This invention relates to a composition for treating herpes and cold sores. More particularly, the invention relates to composition which may be directly applied to herpes and cold sores or may be ingested orally in order to treat the herpes and cold sores. The composition, which contains *olea europaea* leaf extract and *olea europaea* fruit oil, is preferably easy to administer and produce, reduces irritation from herpes and cold sores.

BACKGROUND

For centuries, people have attempted to cure ailments and diseases with whatever compositions, devices, and methods available at the time. Initially, treatment options included rituals or sacred procedures, but as time and civilization progressed, people learned through trial and error the efficacy of certain herbs, roots, and other naturally occurring substances in the treatment of ailments and diseases. Eventually, science has allowed humans to discover why certain herbs and roots are so effective. Useful and effective compounds were identified, isolated, purified, and administered with even great efficacy in the treatment of diseases.

People then discovered they could actually create new or synthetic compounds. With this new creative ability, diseases and viruses were fought on massive scales. As of now, two deadly pathogens, smallpox and rinderpest, appear to have been eradicated, and numerous other diseases are believed to be just a few years away from eradication. Yet, some diseases and viruses have very successful resisted eradication, and are only subject to treatment of the symptoms in order to provide what is, at best, temporary relief.

Herpes, caused by the herpes simplex virus, has been known about for over 2,000 years and has been known to be ubiquitous with some estimates indicating that between 70 and 90% of people will have a cold sore caused by a herpes virus at one point in their life, and approximately 40% of adults will have repeated episodes of cold sore outbreaks. Though normally the virus is not life threatening, it may be dangerous to people with compromised immune systems. There is no known cure for the herpes simplex virus, and currently is treated by focusing on the symptoms, such as controlling the outbreak of sores and soothing irritation caused by the sores.

Some treatments include antiviral drug therapy and/or topical compositions. While there are many types of substances and compositions that are known for treating herpes, the sheer number of different substances that finding a highly effective mixture of the substances to maximize efficacy of the treatment has become a monumental task. The problem with combining substances into a mixed composition is that the results can be hard to predict, and, in many cases, can cause more harm than good. As a result, experimentation must be done slowly and deliberately, and a lot of effort may result in non-useful formulations.

Additionally, some treatment compositions have a list of side effects that may arguably be even worse than the disease itself. For example, valacyclovir, also known as Valtrex®, is one of the most commonly prescribed medications and the side effects include: hives; difficulty breathing; swelling of the face, lips, tongue, or throat; fever; easy bruising or bleeding; red spots on the skin; bloody diarrhea; vomiting; pale or yellowed skin; weakness or fainting; urinating less than usual or not at all; lower back pain; drowsiness; mood changes; increased thirst; loss of appetite; nausea; weight gain; feeling short of breath; confusion; agitation; aggression; hallucinations; trouble concentrating; feeling shaky or unsteady; problems with speech or vision; seizure; stomach pain; headache; dizziness; feeling tired; depression; joint pain; menstrual pain; mild skin rash; stuffy nose; and sore throat. Sometimes it seems as if it is better to have the disease, rather than face the treatment, especially when the treatments have such deleterious side effects.

Further, even though it is known that combining different molecules in a single drug treatment compound is theoretically possible, it is not possible to predict with certainty what the combination may do. Because there are a multitude of biochemical pathways in the body, and studying an entire body is too complex and has too many confounding factors, most experiments are done in vitro under conditions that the experimenter believes may be relevant. Once data is acquired and there is some level of confidence in what the compound actually does, experiments with live patients or other organisms may be started. However, due to the complexity of a fully functioning host, the compound may interfere or react with pathways wholly unaccounted for in the in vitro trials. Even though two molecules appear to act on different biochemical pathways, it is possible that, in combination, they will wholly inhibit a completely different pathway, whereas, when alone, they would only inhibit one part of the pathway which the body could compensate for by using an alternate pathway. Thereby, the pathway in danger of being shut down would be undetected until the two drugs are used in conjunction.

HerbalAlchemist.com sells a balm that includes *hypericum perforatum*, extra virgin olive oil, beeswax, and propolis extract to be used as a general skin salve for irritated skin. Importantly, this references fails to use *olea europaea* leaf extract, *olea europaea* fruit oil or *melaleuca alternifolia* leaf oil. Oleo *europaea* in certain amounts has antiviral activities. *Hypericum perforatum* extract is known to sometimes have bad reactions with certain drugs and drug classes, so it is likely that people are unwilling to experiment with combining *hypericum perforatum* with a potential drug such as *olea europaea*.

European Published Patent Application No. EP2364713, filed by Ilkay Aycan, discloses a composition for treating burns, diseases, and infected wounds. The publication discloses a composition that includes *hypericum perforatum* oil, *melaleuca alternifolia* oil, olive oil, and beeswax Importantly, this reference does not disclose the use of *olea europaea* leaf extract.

U.S. Pat. No. 6,117,844, filed by William Fredrickson teaches the use of *olea europaea* to treat various diseases. One of the diseases taught includes herpes. Importantly, the *olea europaea* taught by Fredrickson is ingested orally or parenterally. The *olea europaea* taught by Fredrickson is also not combined with *hypericum perforatum* extract, propolis extract, or *melaleuca alternifolia* leaf oil Importantly, Fredrickson does not disclose the use of *olea europaea* topically, but teaches that its use should be via ingestion or injection. Also, *hypericum perforatum* extract's properties of having bad interaction with certain classes of drugs may also lead a person of ordinary skill in the art away from combining it with other drugs and anti-viral compositions.

U.S. Pat. No. 8,092,843, filed by Melcher teaches the use of *olea europaea* leaf extract to treat herpes. This reference uses alcoholic extraction to obtain *olea europaea* leaf extract and combines the result with neem, *aloe*, and menthol. Importantly, there is no suggestion or even mention of combining the disclosed composition with any other substances, and there is no mention of *olea europaea* fruit oil, *hypericum perforatum* extract, propolis extract, or *melaleuca alternifolia* leaf extract.

Thus, there exists the need for effective methods and compounds that contain both *olea europaea* leaf extract and *olea europaea* fruit oil, for treating herpes and cold sores.

SUMMARY OF THE INVENTION

To minimize the limitations in the prior art, and to minimize other limitations that will become apparent upon reading and understanding the present specification, the present invention is a composition for treating herpes and other skin conditions, wherein the composition is stabilized, contains *olea europaea* leaf extract and *olea europaea* fruit oil, and is directed to primarily treating skin conditions.

One embodiment of the invention is a herpes treatment composition which preferably comprises one or more therapeutic agents, wherein said therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition.

One embodiment of the invention is a herpes treatment composition which preferably comprises one or more therapeutic agents, wherein, said therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition. Preferably, the herpes treatment composition further comprises one or more skin moisturizers.

Another embodiment of the invention is a herpes treatment composition which preferably comprises one or more therapeutic agents, wherein the therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition. Preferably the herpes treatment composition further comprises one or more emulsifiers.

Another embodiment of the invention is a herpes treatment composition which preferably comprises one or more therapeutic agents, wherein the therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition. Preferably, the herpes treatment composition further comprises one or more stiffeners.

Another embodiment of the invention is a herpes treatment composition which preferably comprises one or more therapeutic agents, wherein the therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition. Preferably, the herpes treatment composition further comprises one or more flavors.

Another embodiment of the invention is a herpes treatment composition which preferably comprises one or more therapeutic agents, wherein the therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition. Preferably, the herpes treatment composition further comprises one or more fixatives.

Another embodiment of the invention is a herpes treatment composition which preferably comprises one or more therapeutic agents, wherein the therapeutic agents preferably comprise an *olea europaea* leaf extract component in an amount of from 0.1 to 0.3 percent by weight based on a total weight of the herpes treatment composition and an *olea europaea* fruit oil component in an amount of from 0 to 0.1 percent by weight based on a total weight of the herpes treatment composition, and preferably further comprises a water component in an amount of from 0 to 99.9 percent by weight based on a total weight of the herpes treatment composition. Preferably, the one or more therapeutic agents further comprises a propolis extract component in an amount of from 0 to 0.1 percent by weight based on a total weight of the herpes treatment composition. Preferably, the therapeutic agents further comprise an *hypericum perforatum* extract component in an amount of from 0 to 0.1 percent by weight based on a total weight of the herpes treatment composition. Preferably, the therapeutic agents further comprises a *maleleuca alternifolia* extract component in an amount of from 9.0 to 50.0 percent by weight based on a total weight of the herpes treatment composition. Preferably, the one or more therapeutic agents further comprises an *aloe barbadensis* leaf juice component in an amount of from 1 to 3 percent by weight based on a total weight of the herpes treatment composition. Preferably, the one or more therapeutic agents further comprises a menthol component in an amount of from 0.1 to 0.2 percent by weight based on a total weight of the herpes treatment composition. Preferably, the one or more therapeutic agents further comprises an allantoin component in an amount of from 0.4 to 0.6 percent by weight based on a total weight of the herpes treatment composition. Preferably, the herpes treatment composition further comprises one or more gelling agents.

Another embodiment of the herpes treatment composition comprises one or more therapeutic agents, wherein the therapeutic agents are comprised of an *olea europaea* leaf extract component and an *olea europaea* fruit oil component. Preferably, the therapeutic agents are combined and used to treat a herpes simplex virus outbreak. Preferably, the *olea europaea* leaf extract component is in an amount of from 0.1 to 0.3 percent by weight; wherein the *olea europaea* fruit oil component is in an amount of less than 0.1 percent by weight based on a total weight of the herpes treatment composition; and wherein the herpes treatment is further comprised of a solvent component in an amount of from 0 to greater than 99.9 percent by weight based on the total weight of the herpes treatment composition. Preferably, the one or more therapeutic agents are further comprised of an *hypericum perforatum* extract component in an amount of less than 0.1 percent by weight based on the total weight of the herpes treatment composition. Preferably, the one or more therapeutic agents are further comprised of a propolis extract component in an amount of less than 0.1 percent by weight based on the total weight of the herpes treatment composition. Preferably, the one or more therapeutic agents are further comprised of a

*maleleuca alternifolia* extract component in an amount from 9.0 to 50.0 percent by weight based on the total weight of the herpes treatment composition. Preferably, the one or more therapeutic agents are further comprised of an *aloe barbadensis* leaf juice component in an amount from 1 to 3 percent by weight based on the total weight of the herpes treatment composition. Preferably, the one or more therapeutic agents are further comprised of a menthol component in an amount from 0.1 to 0.2 percent by weight based on the total weight of the herpes treatment composition. Preferably, the one or more therapeutic agents are further comprised of an allantoin component in an amount from 0.4 to 0.6 percent by weight based on the total weight of the herpes treatment composition. Preferably, the herpes treatment composition further comprises of one or more skin moisturizers. Preferably, the herpes treatment composition further comprises of one or more emulsifiers. Preferably, the herpes treatment composition further comprises of one or more stiffeners. Preferably, the herpes treatment composition further comprises of one or more flavors. Preferably, the herpes treatment composition further comprises of one or more fixatives. Preferably, the herpes treatment composition further comprises of one or more gelling agents.

The herpes treatment composition of claim 9, wherein said therapeutic agents are combined and used to treat a herpes simplex virus outbreak.

It is understood that a herpes simplex virus outbreak may occur when dormant herpes virus in an individual switches into an active phase. In this state an infected individual may experience lesions or painful skin conditions. It is understood that herpes, as used here, includes all types of herpes viruses, including HSV-1, and HSV-2, commonly known as oral herpes and genital herpes, respectively. Oral herpes may also be known as cold sores or fever blisters. It is understood that an outbreak may or may not have a trigger. The trigger may include environmental factors, physiological factors, and other currently unknown factors.

It should be understood that other ingredients may be added to the composition without deviating from the scope or purpose of the composition, so long as those other ingredients do not detract from the efficacy of the composition.

In other embodiments of the invention, additional ingredients may be added to the composition, including, but not limited to, any moisturizer, any emulsifier, any stiffener, any flavor, any fixative, any humectant, any emollient, any penetration enhancer, and any gelling agent.

It should be understood that a therapeutic agent includes anything which may improve the health of one's skin, help fight a disease, treat a viral condition, or treat a skin condition.

It should be understood that the composition preferably may be presented as a solid, a liquid, a spray (liquid, powder, or vapor), an inhalant, and/or a gel. The therapeutic agent is preferably topical, but may be taken in any manner, including by ingestion. The form of the composition is preferably determined by replacing non-therapeutic agents (or ingredients) with other non-therapeutic agents. For example, a solid embodiment, or lip balm, could be created by reducing the amount of water and introducing stiffening agents, or agents which allow a solid to smear upon application. A gel embodiment is preferably similar to a liquid embodiment with the addition of gelling agents to increase viscosity. An ingestible embodiment preferably excludes non-therapeutic agents. An ingestible embodiment is preferably in pill form for easy carrying. An ingestible embodiment may also be a liquid, such that it is consumed in a similar fashion to cough syrups.

It is an object of the present invention to overcome the limitations of the prior art.

Another object of the present composition is to provide people with relief from herpes, cold sores, fever blisters, canker sores, irritated gums, dry skin, and itchy skin.

Another object of the present composition is to prevent people from having herpes and cold sore outbreaks.

Additional embodiments of the invention will be understood from the detailed description of the invention.

DETAILED DESCRIPTION OF THE INVENTION

In the following detailed description of various embodiments of the invention, numerous specific details are set forth in order to provide a thorough understanding of various aspects of one or more embodiments of the invention. However, one or more embodiments of the invention may be practiced without some or all of these specific details. In other instances, well-known methods, procedures, and/or components have not been described in detail so as not to unnecessarily obscure aspects of embodiments of the invention.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the figures, and the detailed descriptions thereof, are to be regarded as illustrative in nature and not restrictive. Also, the reference or non-reference to a particular embodiment of the invention shall not be interpreted to limit the scope of the invention.

The present invention reduces the pain and eases the suffering of people with herpes, cold sores, and various other types of skin and viral diseases or irritations.

The composition utilizes various therapeutic agents in a combination that, heretofore, has never before been combined.

Table 1 shows a preferred composition of one embodiment of the invention. The ingredients are combined to create a herpes and cold sore fighting composition that may take various shapes and forms depending on which additional ingredients are used. The Table also lists the preferred weight (Wt) percentage (%) range of each ingredient and the primary purpose of the ingredient. The composition of Table 1 results in a topical gel, which is preferably applied directly to the skin.

TABLE 1

| Ingredient | Preferred Wt % Range | Purpose |
| --- | --- | --- |
| Water | 30 to >99.9 | Solvent or medium for application |
| Olea Europaea (Olive) Leaf Extract | 0.1 to 0.3 | Active ingredient |
| Olea Europaea (Olive) Fruit Oil | <0.1 | Active ingredient; Emulsifier; Increases transdermal penetration |
| Glycerin | 1 to 3 | Improves smoothness, increases transdermal penetration |
| Aloe Barbadensis Leaf Juice | 1 to 3 | Soothes and helps heal various skin conditions |
| Xanthan Gum | 1 to 3 | Stabilizer |
| Hydroxyethylcellulose | 1 to 3 | Gelling and thickening agent |
| Allantoin | 0.5 | Moisturizer and keratolyzer |
| Carrageenan | 0.1 to 0.3 | Gelling and thickening agent |
| Menthol | 0.12 | Local anesthetic, increases transdermal penetration |

TABLE 1-continued

| Ingredient | Preferred Wt % Range | Purpose |
|---|---|---|
| Glucose | <0.1 | Thickening agent; Preservative |
| Propolis Extract | <0.1 | Sealant for small openings and antimicrobial |
| Hypericum Perforatum Extract | <0.1 | Serotonin increaser, active ingredient, anti-inflammatory |
| Panthenol | <0.1 | Humectant, emollient, and moisturizer |
| Glucose Oxidase | <0.1 | Oxidizer; Preservative |
| Lactoperoxidase | <0.1 | Antibacterial agent; Preservative |

This particular embodiment of the invention is preferably a gel, which may be applied topically. Due to the thickening agents, this embodiment can be excreted from a tube or container and spread onto the affected area of a user's skin, much like a lotion might be applied. This has the advantage over a liquid formulation because a liquid embodiment would be more likely to run and not stay on the affected or applied area due to gravity or the user's movements.

The *olea europaea* leaf extract component is one of the primary active ingredients of the therapeutic composition and preferably acts as an anti-bacterial, anti-viral, and anti-fungal agent. Also, the *olea europaea* leaf extract preferably comprises of a large number of phytochemical components. One important component of the *olea europaea* leaf extract is a phenolic glucoside known as oleuropein. Oleuropein is converted to both the dextrorotary and levorotary forms of elenolic acid by the enzymes esterase and beta-glucosidase. Esterase and beta glucosidase are found in olive trees as well as human blood. The dextrorotary form of elenolic acid does not bind to human blood cells, but the levorotary form of elenolic acid does bind to human blood cells. When the levorotary elenolic acid binds to human blood cells, it becomes ineffective, but does not appear to cause negative side effects.

The molecular structure of oleuropein is:

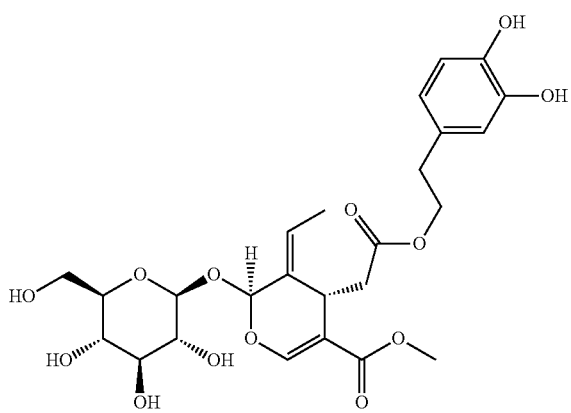 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1]

The molecular structure of elenolic acid is:

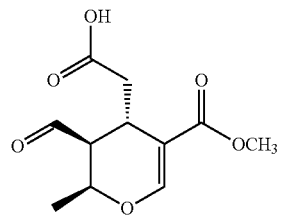 [SMILES: COC(=O)C1=CO[C@@H](C)[C@@H](C=O)[C@@H]1CC(=O)O]

There are two primary methods of introducing levorotary elenolic acid to an area which requires treatment, transdermally and through the blood stream. When combined with natural or chemical penetration enhancers such as glycerine, *aloe vera*, emu oil, and DMSO, the *olea europaea* extract is able to be used transdermally. In addition to the previously named chemical penetration enhancers, other chemicals may be used, including, but not limited to, alcohols, surfactants, terpenes, and other naturally occurring chemicals.

Additionally, *olea europaea* leaf extract undergoes acid hydrolysis in a human stomach, which then enters the blood stream. Once the *olea europaea* leaf extract enters the blood stream or affected areas through ingestion or transdermal movement, oleuropein is converted to both the dextrorotary and levorotary forms of elenolic acid through esterase and beta glucosidase present in the blood stream.

In addition to the active properties of elenolic acid, the aglycone of oleuropein released when elenolic acid is created has inhibitory properties as well. Both the aglycone and the elenolic acid promote phagocytosis. Phagocytosis is the process by which immune system cells or other bacterial cells consume adjacent cells and nutrients. In the case of the herpes virus, increased phagocytotic behavior of the immune system is able to aid in healing the stratum basale of the epidermis.

Elenolic acid, aside from having promoting phagocytotic behavior, also interferes with the transcriptase of the herpes virus. It is believed that the interference is caused by dissolving the outer protein coating of the virus, which may halt infection and spread of the virus by preventing virus budding or shedding. Additionally, it is theorized that elenolic acid can penetrate infected cells directly and stop viral replication without affecting the host cell.

Two derivatives of elenolic acid, 2 epielenolic acid and 6 epielenolic acid have similar in vivo antimicrobial effects as elenolic acid. Preferably, the *olea europaea* leaf extract component is in an amount up to 0.3 percent by weight, and more preferably between 0.1 to 0.3 percent by weight.

The *olea europaea* fruit oil component is one of the primary ingredients of the therapeutic composition and preferably acts as an emulsifier, stabilizer, preservative, transdermal enhancer, and an active ingredient. Because *olea europaea* leaf extract may be unstable under certain conditions, the *olea europaea* fruit oil acts as a preservative, keeping the *olea europaea* leaf extract viable and useful for longer periods of time. Additionally, *olea europaea* fruit oil enhances the ability of the *olea europaea* leaf extract to act transdermally. Furthermore, *olea europaea* fruit oil contain high amounts of oleuropein and its derivatives and is therefore able to act to increase the effectiveness of the composition, similarly to the way *olea europaea* leaf extract functions. *Olea europaea* fruit oil also comprises erythrodiol, beta-sitosterol, squalene, tyrosol, hydroxytyrosol, and caffeic acid which may aid in *olea europaea* fruit oil's biological properties. Preferably, the *olea*

*europaea* fruit oil component is in an amount up to 0.1 percent by weight, and more preferably between 0 to 0.1 percent by weight.

The *hypericum perforatum* extract component preferably. *Hypericum perforatum* is a member of the genus *Hypericum*, also known as St. John's Wort. The *hypericum perforatum* extract preferably acts as an anti-inflammatory, anti-viral, anti-bacterial, and anti-fungal agent. Typically, *hypericum perforatum* extract becomes a monoamine oxidase inhibitor when consumed and is commonly used for major depressive episodes. Preferably, when used topically, the hyperforin component of the *hypericum perforatum* extract constitutes its anti-bacterial and anti-inflammatory effects. Preferably, when used topically, the hypericin and pseudohypericin components of *hypericum perforatum* extract act as an anti-viral and anti-bacterial activities. It is currently believed that the hyperforin and hypericin bind non-specifically to viral and cellular membranes and can result in oxidation of the pathogens to kill the pathogens. Preferably, *hypericum perforatum*, when applied topically, is able to calm nerves in the epidermis by blocking certain sensory receptors. *Hypericum perforatum* has been known to be harmful if ingested with other drugs or medications. Specifically, *hypericum perforatum* has been known to interact with amphetamines, asthma inhalants, decongestants, diet pills, narcotics, the amino acids tryptophan and tyrosine, and certain foods. Other *hypericum* species have been recorded as being anti-viral, some examples of which comprise: *hypericum connatum*; *hypericum mysorense*; *hypericum hookerianum*; *hypericum crispum* L; and individual species of *hypericum* for Nepal. Preferably, the *hypericum perforatum* component is in an amount up to 0.1 percent by weight, and more preferably between 0 to 0.1 percent by weight.

Water is used as a suitable medium for adequately dissolving all the components of one embodiment of the composition. The water is preferably demineralized and deionized, but is not limited thereto. The viscosity and various other properties of the water are modified by the addition of other components. Preferably, the water component is in an amount up to 99 percent by weight, and more preferably between 30 to 95 percent by weight. Other mediums may be used without deviating from the scope of the invention.

The glycerin component is optional and preferably helps to improve smoothness of the gel embodiment. Glycerin also acts as a humectant, which helps the composition to retain water. Additionally, glycerin aids in applying the *olea europaea* extract transdermally by taking surrounding elements of the *olea europaea* extract and other components of the composition as substrate. Then the glycerin penetrates the epidermis with the *olea europaea* extract. Preferably, the glycerin component is in an amount up to 3 percent by weight, and more preferably between 1 to 3 percent by weight.

The molecular structure of glycerin is:

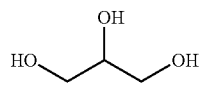

The *aloe barbadensis* leaf juice component is optional and preferably helps decrease wound healing time. *Aloe barbadensis* leaf juice also preferably helps in the treatment of herpes. *Aloe barbadensis* leaf juice is extracted from the *Aloe Vera* plant. *Aloe barbadensis* leaf juice preferably acts as an antibacterial and antifungal agent, to prevent open wounds, cold sores, or herpes outbreaks from becoming further infected. Preferably, the *aloe barbadensis* leaf juice component is in an amount up to 3 percent by weight, and more preferably between 1 to 3 percent by weight.

The xanthan gum component is optional and preferably increases the viscosity of the composition, even if only small amounts of the xantham gum are used. Preferably, the xanthan gum component is in an amount up to 3 percent by weight, and more preferably between 1 to 3 percent by weight.

The molecular structure of xanthan gum is:

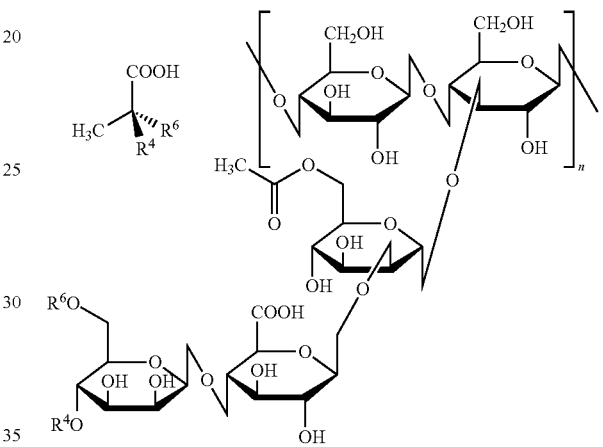

The hydroxyethylcellulose component is optional and preferably serves two functions. The first function is to thicken the composition. The second function is to increase the dissolution of the drug. Preferably, the hydroxyethylcellulose xanthan gum component is in an amount up to 3 percent by weight, and more preferably between 1 to 3 percent by weight.

The molecular structure of hydroxyethylcellulose is:

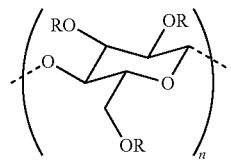

R = H or CH$_2$CH$_2$OH

The carrageenan component is optional and preferably functions to thicken and gel the agent. Carrageenan is extracted from red seaweed and is a common thickening agent used in cooking. Preferably, the carrageenan component is in an amount up to 0.3 percent by weight, and more preferably between 0.1 to 0.3 percent by weight.

The menthol component is optional and preferably functions as a local anesthetic, to help soothe the affected area. Additionally, the menthol component also increases transdermal penetration. Preferably, the menthol component is in an amount up to 0.15 percent by weight, and more preferably between 0.1 to 0.15 percent by weight.

The molecular structure of menthol is:

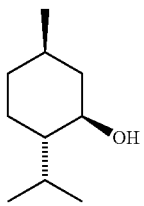

The propolis extract component is optional and preferably functions as sealant and antimicrobial agent. Propolis extract is a mixture collected by honey bees from botanical sources and used as a sealant in hives. This preferably assists in healing the open wound and preventing new infections. Preferably, the propolis extract component is in an amount up to 0.1 percent by weight, and more preferably between 0 to 0.1 percent by weight.

The panthenol component is optional and preferably acts as a humectant, emollient, and moisturizer. This preferably allows the composition to retain more water and help the composition reduce its harshness. Preferably, the panthenol component is in an amount up to 0.1 percent by weight, and more preferably between 0 to 0.1 percent by weight.

The molecular structure of panthenol is:

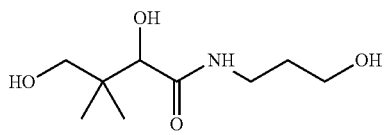

The glucose oxidase component preferably acts as a reducing agent. Glucose oxidase may be used as a product stabilizer. Additionally, glucose oxidase may be used in conjunction with lactoperoxidase and glucose, as explained below. Preferably, the glucose oxidase component is in an amount up to 0.1 percent by weight, and more preferably between 0 to 0.1 percent by weight.

The glucose component is optional and preferably is converted to hydrogen peroxide by the catalyst glucose oxidase. Preferably, the glucose component is in an amount up to 0.1 percent by weight, and more preferably between 0 to 0.1 percent by weight.

The molecular structure of glucose is:

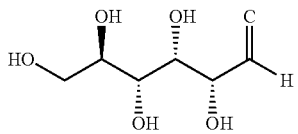

The lactoperoxidase component is optional and preferably acts as a preservative when used in combination with glucose oxidase and glucose. After the glucose oxidase has converted the glucose to hydrogen peroxide, the lactoperoxidase is able to use the hydrogen peroxide to oxidize various substrates including, but not limited to, iodide and thiocyanate which creates a strong anti-bacterial agent. Lactoperoxidase is secreted from mammary, salivary, and other mucosal glands and functions as a natural antibacterial agent. Because one embodiment of the current invention is utilized in the lip and mouth area, saliva is likely to be present, and saliva contains hypothiocyanite ions (OSCN—) which may be used with the lactoperoxidase enzyme. Additionally, lactoperoxidase has antibacterial properties for skin and may be helpful for eliminating acne-causing bacteria. Furthermore, lactoperoxidase is commonly used as a product stabilizer, as may its function be here. Lactoperoxidase also plays an important role in the innate immune system by killing bacteria in milk and mucosal secretions. This activity may also be helpful in treating herpes and cold sores. Preferably, the lactoperoxidase component is in an amount up to 0.1 percent by weight, and more preferably between 0 to 0.1 percent by weight.

It should also be understood that effective amounts of other compatible substances such as dyes or colorants, fragrances, and preservatives may also be added to the herpes and cold sore fighting composition based on the total weight of the composition.

Although specific compounds are listed in Table 1, it should be understood that equivalent compounds may be used. Preferably, the current invention utilizes various phytochemicals as biocidal agents. In several preferred embodiments of the present invention, *olea europaea* leaf extract, *olea europaea* fruit oil, lactoperoxidase, and *aloe barbadensis* extract may be used as biocidal agents. Other phytochemical and biocidal agents that may be used comprise: *Jasonia candicans* (sesquiterpenes, lactones); *Polygonum flaccidum* (flavone and alpha santalene derivatives); *Acalypha wikesiana* (extracts); *Pavetta owariensis* (procyanidins); *Plectranthus hereroensis* (diterpenoids, diterpenes); Moss (Dicranin extract); *Cannabis sativa* (extract); *Gloiosiphonia* spp. (gloiosiphones); Laminaceae spp. (extract); *Securidaca* spp. (extract); *Veronia* spp. (extract); *Hyptis umbrose* (umbrosone); *Asclepias syriaca* (milkweed extract); *Tagetes tenuifolia* (thiophene); *Calophyllum inophylloide* (flavonoids); *Tanacetum densum* (sesquiterpene lactones, triterpenoids); *Neorautanenia mitis* (extract); *Premna schimper* (diterpene); *Premna oligotricha* (sesquiterpenes); *Premna oligotricha* (diterpenes); *Jasonia candicans* (essential oils); *Visnea mocanera* (beta-sitosterol, triterpenic betulinic acid, ursolic acid, plantanic acid); Asteraceae spp. (terthiophenes and polyynes); *Petalostemum purpureum* (extract); *Camelia sinensis* (catechin); *Helichrysum picardii* (flavonoids); *Helichrysum italicum* (flavonoids); *Corydalis pallida* (protoberberine alkloids); *Shiraia bambusicola* (perylenequinones); *Fraxinum omus* (hydroxycoumarins); *Podocarpus nagi* (totarol and nortiterpene dilactones); *Heterotheca inuloides* (sesquiterpenoids); *Pelargonium* spp. (essential oils); *Piper sarmentosum* (phenylpropanoids); *Allium* spp. (extract); *Juniperus procera* (diterpenes); *Achillea conferta* (flavonoids, flavones, sesquiterpenoid lactones); *Magnolia virginiana* (lignans, neolignans); *Eucalyptus euglobal* (euglobal); *Armillaria mellea* (armillaric acid); *Dracena mannii* (spirostanol saponin); *Piper aduncum* (chromenes, prenylated benzoic acid); Rhamnaceae spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); *Paepalanthus* spp. (vioxanthin); *Helichrysum stoechas* and *Helichrysum crispum* (extracts); *Achillea ptarmica* (trans-pinocarveyl hydroperoxides); *Dehaasia incrassata* (alkaloids); Asteraceae spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative), *Celosia argentea* (triterpenoid saponins and flavonoids); *Azadirachta indica* (tetranortriterpenoid, mahmoodin, protolimonoids, naheedin); Moraceae spp. (coumarins); *Hypericum erectum* (phloroglucinol derivatives); *Podospora appendiculate* (Appenolides A, B, & C, furanones); *Artemisia princeps* var. *orientalis*, *Artemisia capillaris*, *Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borrieria latifolia*, *Borreria setidens*, *Hedyotis diffusa*), *Hedyotis nudicaulis*, *Morinda elliptica*, *Morinda umbellata*, *Sida rhombifolia*, and *Vitex ovata* (extracts); *Tabebuia impetiginosa*, *Achyrocline* spp., *Larrea divaricata*, *Rosa borboniana*, *Punica granatum*, *Psidium guineense*, *Lithrea ternifolia* (extracts); *Lepechinia caulescens*, *Lepidium virginicum* and *Tanacetum parthenium* (extracts); *Talaromyces flavus* (extracts); *Daucus carota* (extract); *Flabellia petiolata*, *Caulerpa prolifera*, *Halimeda tuna*, *Corallina elongata*, *Lithophyllum lichenoides*, *Phyllophora crispa*, *Cystoseira* spp., *Halopteris* spp., *Codium* spp., *Valonia utricularis*, *Posidonia oceanica*, *Zostera noltil* and *Cymodocea nodosa* (extracts); *Centauraea orientalis*, *Diospyros khaki*, *Sida hermaphrodita*, *Forsythia intermedia*, *Scutellaria polydon*, *Eugenia malaccensis* and *Eugenia jambolana* (extracts); *Fritillaria* L. spp. (ebeinone, steroidal alkaloids); *Kigelia pinnata*, *Peperomia pellucida*, *Populus nigra*, *Populus balsamifera* and *Populus deltoides* (extracts); *Melaleuca alternifolia* (essential oil); *Elfvingia applanata* (naringenin); *Ficus sycomorus*, grapefruit seed, Garlic, Allicin, Peat, *Strophanthus hispidus*, *Secamone afzeli*, *Mitracarpus scaberi*, *Entada abyssinjca*, *Terminalia spinosa*, *Harrisonia abyssinica*, *Ximinea caffra*, *Azadirachta indica*, *Spilanthes mauritiana*, *Terminalia spinosa* (extracts); *Cyanobacteria* (ambigols A and B, tjipanazole); coffee (extract); *Sporochnus pedunculatus*, *Dalbergia melanozylon*, *Celastrus scandens*, *Juglans nigra*, *Kalmia latifolia*, *Pelargonium xhortorum*, *Rhus glabra* and *Lindera benzoin* (extracts); *Striga densiflora*, *Striga orobanchioides*, *Striga lutea*, *Pistacia lentiscus* L., *Mitracarpus villosus*, *Bixa orellana*, *Bridelia ferruginea*, *Alpinia katsumadai*, *Alpinia officinarum*, *Artemisia capillaris*, *Casia obtusifolia*, *Dendrobium moniliforme*, *Epimedium grandiflorum*, *Glycyrrhiza glabra*, *Lithosperum erythrorhizon*, *Magnolia obovata*, *Mortis bonbycis*, *Natopterygii incisium*, *Polygonum multiflorum*, *Prunus mume*, *Rheum palmatum*, *Ricinus communis*, *Sophora flavescens*, *Swertia japonica*, black pepper, rosemary, red pepper, *Isopyrum thalictroides*, *Calotropis procera*, *Chrysanthemum* spp., *Holarrhena antidysenterica*, *Lunularia crusiata*, *Dumertiera hirsuta*, *Exormotheca tuberifera*, and liverwort (extracts); *Filipendula ulmaria*, *Salix glauca*, *Usnea filipendula*, *Clkadina arbuscula* (salicylic compounds); *Tanacetum parthenium*, *Thymus capitatus*, and *Elfingia applanata* (extracts); *Fraxinus ornus* (hydroxycoumarins, esculin, esculetin, fraxin, and fraxetin); *Zizyphus nummularia*, LONGO VITAL, *Pelargonium* spp., *Scaevola sericea*, *Psychotria hawaiiensis*, *Pipturus albidis*, *Aleurites moluccana*, *Solanum niger*, *Piper methysticum*, *Barringtonia asiatica*, *Adansonia digitata*, *Harungana madagascariensis*, *Jacaranda mimosaefolia*, *Erythroxylum catauba*, *Bidens pilosa*, *Lemna minor*, *Potamogeton* spp., *Nasturtium officinale*, *Apium nodiflorum*, *Agaricus subrutilescens*, *Amanita virosa*, *Amanita pantherina*, *Lycoperdon perlatum*, *Psidium guajava*, *Averrhoa carambola*, *musa sapientum*, *Carica papaya*, *Passiflora edulis*, *Lansium domesticum* and *Baccaurea motleyana* (extracts); horse radish, celandine grass, bur marigold and yarrow grass (extracts); *Abuta grandifola*, *Cyperus articulatus*, *Gnaphalium spicatum*, *Pothomorphe peltata*, *Ficus sycomorus*, *Ficus Benjamina*, *Ficus bengalensis*, *Ficus religiosa*, *Alchornea cordifolia*, *Bridelia feruginea*, *Eucalyptus citriodora*, *Hymenocardia acida*, *Maprounea africana*, *Monachora arbuscula*, *Tedania ignis*, *Arenosclera* spp., *Amphimedon viridis*, *Polymastia janeirensis*, *Aplysina fulva*, *Pseudaxinella lunaecharta*, *Nelumbium speciosum* and *Mycale arenosa* (extracts); cloves (eugenol acetate and isoeugenol); *Chrysthanemum boreale* (sesquiterpenoid lactones); *Eucalyptus globolus*, *Punica granatum*, *Bocconia arborea*, *Syzygium brazzavillense*, *Syzygium guineense*, *Carthamus tinctorius*), *Ginkgo biloba*, *Mosla chinensis*, *Salvia officinalis*, and *Cinnamomum cassia* (extracts); *Cryptolepis sanguinolenta* (alkaloids, cryptolepine); *Chelidonium majus* (alkaloids, berberine, coptisine); *Vitex agnus-castus* (extract); *Cladonia substellata* (usnic acid); *Fuligo septica*, *Tubifera microsperma* (extract); *Mundulea monantha*, *Tephrosia linearis* (flavonoids); *Lpomoea fistulosa* (extract); *Pimenta dioica* (essential oils); *Ratibida latipalearis*, *Teloxys graveolens*, *Dodonaea viscosa*, *Hypericum calycinum*, *Hyptis albida*, *Hyptis pectinata*, *Hyptis suaveolens* and *Hyptis verticillata* (extracts); *Asteriscus graveolones* (bisabolone hydroperoxides); *Derris scandens*, *Alnus rubra*, Araliaceae family (extracts); *Vinca rosea*, Australian tea tree oil, peppermint oil, sage oil, thymol, eugenol and *Thuja orientalis* (extracts); *Anacardium occidentale* (phenolic lipids); *Oidiodendron tenuissimum* (extract); *Acacia nilotica* and *Acacia farnesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla*, *Chamaesyce hirta*, *Baccharis glutinosa* and *Larrea tridentata* (extracts); *Camelia sinensis* and *Euphorbia hirta* (theaflavin, polyphenon 60); *Tabemaemontana pandacaqui*, *Yucca shidigera*, *Hemistepa lyrata*, *Yougia japonica*, *Prunella vulgaris*, *Lamium amplexicaule*, *Juniperus chinensis*, *Ixeris dentata*, *Gnaphalium affine*, *Chelidonium majus*, *Spirea prunifolia*, *Erythronium japonicum*, *Taxus wallichiana*, *Ganoderma lucidum Drava nemorosa*, *Youngia capillaris*, *Equisetum arvense*, *Australiam Lavender*, Black Seed, *Catuaba casca*, Cineole, Damiana, *Dicranum scoparium*, Eucalyptus oil, Ginger, and Grape seed (extracts); Neem seed, bark, and leaf extract; Neem oil; New Zealand Manuka extract; *Nicotiana tabacum* extract; a-pinene and b-pinene extracts; Rhubarb root extract; *Syringa vulgaris* extract; Tea tree oil (Terpinen-4-ol, a-terpinene, y-terpinene, a-terpineol, Terpinolene); Thyme (extract) and Vitamin E (extract).

Additionally, various chemicals may be used to increase the transdermal penetration, the chemicals comprising: cineole; eucalyptol; propylene glycol; emu oil; DMSO; certain alcohols; surfactants; terpenes; vitamin E acetate; vitamin A palmitate; palmitic acid; sea buckthorn oil; coca butter; pumpkin oil; avocado oil; coconut oil; panthenol; lemon balm; melidda *officinalis*; red marine algae—variety *gigartina skottsbergii*; argan oil; *croton lechleri muell*; and *maleleuca alternifolia* extract or oil.

The composition of the present invention may be made using a mixing process. Preferably, gelling and thickening agents are added last, to allow for easy mixing. One possible method of preparing the *olea europaea* leaf extract is by the method disclosed by U.S. Pat. No. 6,117,844, issued to William Frederickson, the contents of which are expressly incorporated herein by this reference as though set forth in their entirety.

Alternatively, a tablet or capsule may be used. The tablet or capsule would range from about 500 mg to 1000 mg and comprise: *olea europaea* leaf extract; *ribes nigrum*; red marine algae; and naringin.

Although herpes and cold sores are the typical target of the current herpes and cold sore treatment composition, it should be understood that the present invention may be used to fight a wide variety of skin related conditions.

Using the composition or method of the present invention allows a user to have another option in fighting herpes and cold sores. The quality of life of a user may be increased if the composition is effective.

The foregoing description of the preferred embodiment of the invention has been presented for the purposes of illustration and description. While multiple embodiments are disclosed, still other embodiments of the present invention will become apparent to those skilled in the art from the above detailed description, which shows and describes illustrative embodiments of the invention. As will be realized, the invention is capable of modifications in various obvious aspects, all without departing from the spirit and scope of the present invention. Accordingly, the detailed description is to be regarded as illustrative in nature and not restrictive. Also, although not explicitly recited, one or more embodiments of the invention may be practiced in combination or conjunction with one another. Furthermore, the reference or non-reference to a particular embodiment of the invention shall not be interpreted to limit the scope the invention. It is intended that the scope of the invention not be limited by this detailed description, but by the claims and the equivalents to the claims that are appended hereto.

What is claimed is:

1. A herpes treatment capsule consisting essentially of therapeutically effective amounts of *olea europaea* leaf extract, *olea europaea* fruit oil, *hypericum performatum* extract, propolis extract and *maleluca alternifolia* extract.

2. A herpes treatment pill consisting essentially of therapeutically effective amounts of *olea europaea* leaf extract, *olea europaea* fruit oil, *hypericum performatum* extract, propolis extract and *maleluca alternifolia* extract.

3. A herpes treatment tablet consisting essentially of therapeutically effective amounts of *olea europaea* leaf extract, *olea europaea* fruit oil, *hypericum performatum* extract, propolis extract and *maleluca alternifolia* extract.

* * * * *